(12) United States Patent
Das Gupta et al.

(10) Patent No.: US 7,569,537 B2
(45) Date of Patent: Aug. 4, 2009

(54) PEPTIDE ANTAGONISTS FOR INHIBITING HEAT SHOCK PROTEIN (HSP 16.3) OF *MYCOBACTERIUM TUBERCULOSIS*

(75) Inventors: Sujoy K. Das Gupta, Kolkata (IN); Abhik Saha, Kolkata (IN); Archna Pathak Sharma, Kolkata (IN); Siddhartha Roy, Kolkata (IN); Bhabatarak Bhattacharya, Kolkata (IN); Pinakpani Chakrabarti, Kolkata (IN)

(73) Assignee: Council of Scientific and Industrial Research (IN)

( * ) Notice: Subject to any disclaimer, the term of this patent is extended or adjusted under 35 U.S.C. 154(b) by 146 days.

(21) Appl. No.: 10/854,421

(22) Filed: May 26, 2004

(65) Prior Publication Data

US 2007/0037211 A1 Feb. 15, 2007

(51) Int. Cl.
*A01N 37/18* (2006.01)
*A61K 38/00* (2006.01)
*C07K 2/00* (2006.01)
*C07K 4/00* (2006.01)
*C07K 7/00* (2006.01)
*C07K 14/00* (2006.01)
*C07K 16/00* (2006.01)
*C07K 17/00* (2006.01)

(52) U.S. Cl. .............................. 514/2; 530/300; 530/333
(58) Field of Classification Search ........................ None
See application file for complete search history.

(56) References Cited

U.S. PATENT DOCUMENTS 6,403,100 B1 6/2002 Barry et al.

OTHER PUBLICATIONS

Betts, J.C., Lukey, P.T., Robb, L.C., McAdam, R.A., and Duncan, K. Evaluation of a nutrient starvation model of *Mycobacterium tuberculosis* persistence by gene and protein expression profiling. Mol. Microbiol. 43(3), 717-731 (2002).
Chang, Z., Primm, T.P., Janaka, J., Lee, I.H., Serysheva, I., Chiu, W., Gilbert, H.F., and Quiocho, F.A. *Mycobacterium tuberculosis* 16-kDa antigen (Hsp16.3) functions as an oligomeric structure in vitro to suppress thermal aggregation. J. Biol. Chem. 271(12), 7218-7233 (1996).
Coates, A., Hu, Y., Bax, R., and Page, C. The future challenges facing the development of new antimicrobial drugs. Nat. Rev. Drug Discov. 1(11), 895-910 (2002).
Dye, C., Scheele, S., Dolin, P., Pathania, V., and Raviglione, M.C. Consensus statement. Global burden of tuberculosis: estimated incidence, prevalence, and mortality by country. WHO Global Surveillance and Monitoring Project. JAMA 282, 677-686 (1999).

Lee, B.Y., Hefta, S.A., and Brennan, P.J. Characterization of the major membrane protein of virulent *Mycobacterium tuberculosis*. Infect. Immun. 60, 2066-2074 (1992).
Otvos, L. Jr., O, I., Rogers, M.E., Consolvo, P.J., Condie, B.A., Lovas, S., Bulet, P., and Blaszczyk-Thurin, M. Interaction between heat shock proteins and antimicrobial peptides. Biochemistry 39, 14150-14159 (2000).
Sherman, D.R., Voskuil, M., Schnappinger, D., Liao, R., Harrell, M.I., and Schoolnik, G.K. Regulation of the *Mycobacterium tuberculosis* hypoxic response gene encoding alpha-crystallin. Proc. Natl. Acad. Sci. USA 98(13), 7534-7539 (2001).
Stewart, G.R., Robertson, B.D., and Young, D.B. Tuberculosis: A problem with persistence. Nature Reviews—Microbiology 1, 97-105 (2003).
Valdez, M.M., Clark, J.I., Wu, G.J.S., and Muchowski, P.J. Functional similarities between the small heat shock proteins *Mycobacterium tuberculosis* Hsp16.3 and human alphaB-crystallin. Eur. J. Biochem. 269, 1806-1813 (2002).
Verbon, A., Hartskeerl, R.A., Schuitema, A., Kolk, A.H.J., Young, D.B., and Lathigra, R. The 14,000- molecular-weight antigen of *Mycobacterium tuberculosis* is related to the alpha-crystallin family of low-molecular-weight heat shock proteins. J. Bacteriol. 174(4), 1352-1359 (1992).
Yuan, Y., Crane, D.D., and Barry, III, C.E. Stationary phase-associated protein expression in *Mycobacterium tuberculosis*: function of the mycobacterial alpha-crystallin homolog. J. Bacteriol. 178 (15), 4484-4492 (1996).
Yuan, Y., Crane, D.D., Simpson, R.M., Zhu, Y., Hickey, M.J., Sherman, D.R., and Barry, III, C.E. The 16-kDa alpha-crystallin (Acr) protein of *Mycobacterium tuberculosis* is required for growth in macrophages. Proc. Natl. Acad. Sci. USA 95, 9578-9583 (1998).

*Primary Examiner*—Robert B Mondesi
*Assistant Examiner*—Oluwatosin Ogunbiyi
(74) *Attorney, Agent, or Firm*—Summa, Additon & Ashe, P.A.

(57) ABSTRACT

A process to identify peptide antagonists of Hsp16.3, a chaperon protein necessary for the survival of *Mycobacterium tuberculosis* in the dormant phase is described. Affinity selection of a 7-mer and a 12-mer random peptide libraries displayed on bacteriophage M13 was performed using recombinant Hsp16.3 as template and two peptide phage clones, which bind to the Hsp16.3 protein were identified. Synthetic peptides corresponding to the peptide sequences displayed on these phage clones were able to specifically bind and inhibit the chaperone function of Hsp16.3 in vitro in a dose dependent manner. The corresponding inhibitory effect of these peptides on the chaperon activity of alphaB-crystallin, a constituent of human eye lens and a homologue of Hsp16.3, was found to be substantially less. These peptide inhibitors, or similar inhibitors generated by the process described, which specifically target Hsp16.3, can hence be used as lead compounds to obtain better therapeutics against latent *tuberculosis*.

3 Claims, 7 Drawing Sheets

Figure 1:
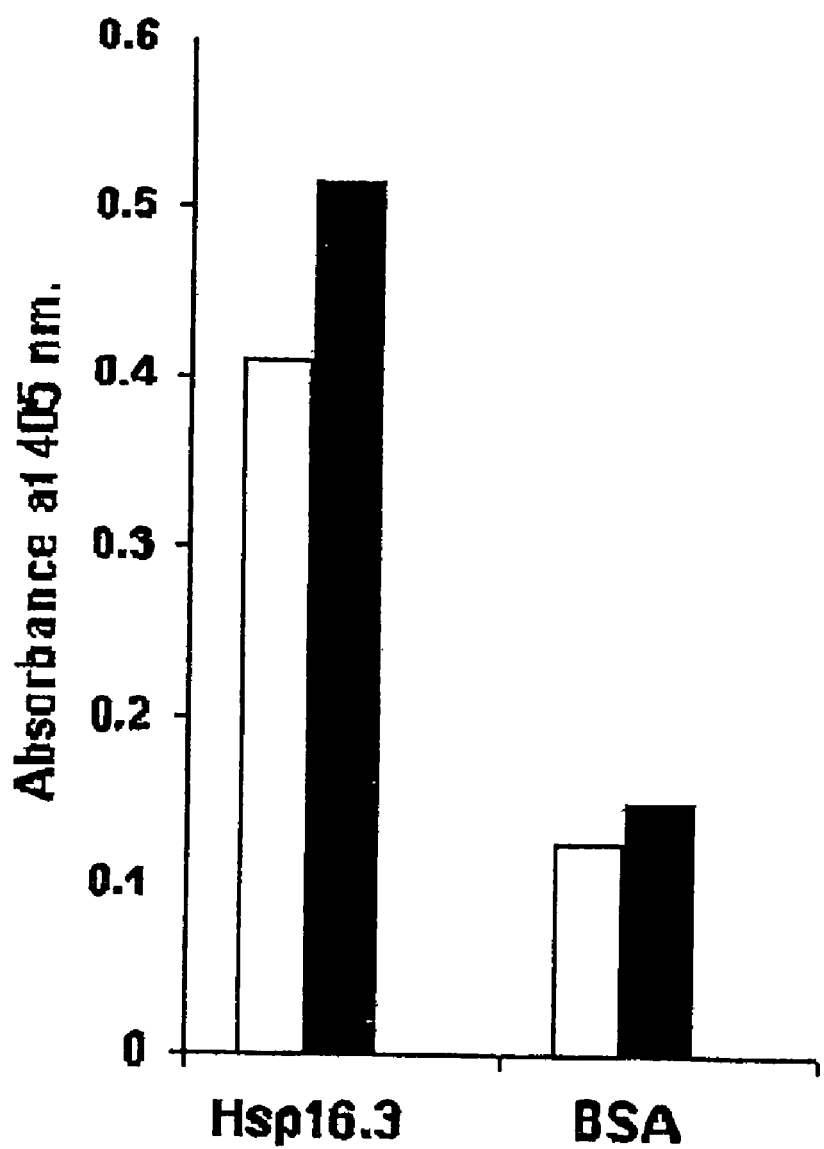

```
                            SEQUENCE LISTING

<160> NUMBER OF SEQ ID NOS: 2

<210> SEQ ID NO 1
<211> LENGTH: 11
<212> TYPE: PRT
<213> ORGANISM: Artificial
<220> FEATURE:
<223> OTHER INFORMATION: peptide antagonist

<400> SEQUENCE: 1

Lys Met His Ala Thr Asn His Gly Gly Gly Ser
1               5                   10

<210> SEQ ID NO 2
<211> LENGTH: 16
<212> TYPE: PRT
<213> ORGANISM: artificial
<220> FEATURE:
<223> OTHER INFORMATION: peptide antagonist

<400> SEQUENCE: 2

Tyr Pro His His Phe Lys His Arg His Ile Pro Ile Gly Gly Gly Ser
1               5                   10                  15
```

PEPTIDE ANTAGONISTS FOR INHIBITING HEAT SHOCK PROTEIN (HSP 16.3) OF MYCOBACTERIUM TUBERCULOSIS

This application incorporates by reference the sequence listing submitted herewith on paper. This paper copy of the sequence listing is entitled "Sequence Listing".

FIELD OF THE INVENTION

The present invention provides peptide antagonists of Hsp16.3, a chaperon protein necessary for the survival of *Mycobacterium tuberculosis* in the dormant phase is described. Affinity selection of a 7-mer and a 12-mer random peptide libraries displayed on bacteriophage M13 was performed using recombinant Hsp16.3 as template and two peptide phage clones, which bind to the Hsp16.3 protein were identified. Synthetic peptides corresponding to the peptide sequences displayed on these phage clones were able to specifically bind and inhibit the chaperone function of Hsp16.3 in vitro in a dose dependent manner. The corresponding inhibitory effect of these peptides on the chaperon activity of alpha-crystallin, a constituent of human eye lens and a homologue of Hsp16.3, was found to be substantially less. These peptide inhibitors, or similar inhibitors generated by the process described, which specifically target Hsp16.3, can hence be used as lead compounds to obtain better therapeutics against latent tuberculosis.

BACKGROUND OF THE INVENTION

Dormancy and Persistence:

Bacteria require specific conditions for growth. Under ideal conditions they grow exponentially but under limiting conditions they stop dividing. In such conditions bacteria are known to pass into a state where the metabolic activity is minimized. In some bacteria this state is achieved through sporulation but in others a functionally similar state known as dormancy takes over. Dormant bacteria do not give rise to colonies but if incubated under appropriate conditions it is possible to resuscitate them. An important attribute of dormant bacteria is that they are more equipped to persist under adverse conditions, such as during drug therapy, than actively growing bacteria. *Mycobacterium tuberculosis*, the tuberculosis (TB) pathogen, is particularly known to persist in a dormant state for a long time within human hosts. In the context of mycobacterial infections the terms "dormant" and "persistent" are generally used synonymously to describe the non-replicating bacteria. In tuberculosis the term latency is often used. It means that following primary infection an active disease may not develop. The infection may remain latent for a prolonged period of time until at some stage reactivation occurs for reasons that are not clearly known as yet. However there are evidences to show that the latency is closely related to dormancy and persistence.

Chaperon Function:

Proteins are known to have specific functions which arise out of their secondary and tertiary structures. Polypeptides may attain these structures by themselves, but in most cases the process of attaining such structures termed as "folding" is aided by other proteins which are functionally known as "chaperons". The chaperons may not only aid folding but also they may prevent misfolding. The ability to prevent misfolding is important as such misfolded proteins form nonviable aggregates which are lethal to the cell. The ability of chaperons to prevent aggregation can be reproduced in vitro and this is often used as a measure of chaperon activity. In most cases the synthesis of the chaperons is increased several fold by heat shock. The increased synthesis during heat shock is essential as under such conditions proteins are more likely to be denatured. Chaperons are therefore often referred to in a loose sense as "heat shock proteins" or Hsps. Hsps need not always be induced by heat shock. Other shocks such as acid shock, low oxygen tension etc. can also bring about the same effect.

Peptide Inhibitors:

Peptides are polymers of amino acids which are linked through amide bonds. The smallest peptide that can be formed is a di-peptide. Peptides may however be larger comprising of as many as forty amino acids. Peptides can exist in specific conformations and can have biological activity. They may act as hormones, immuno-modulators, antibiotics, antigens, agonists as well as antagonists of various functions. The ability to synthesize peptides chemically and incorporate within them uncommon amino acids make them useful systems for obtaining novel bio-active molecules. Because of their conformational flexibility peptides can mimic the structures of natural ligands. Such peptide mimics can be used as inhibitors of biological processes.

Lead Compounds:

Present day drug development processes employ either random high-throughput techniques or structure based drug design methods. In either case the initial screens lead to compounds that cannot be used directly as drugs but they can be potentially developed further after studying the manner in which they interact with the target. In other words an initial low affinity interaction can be converted to a high affinity interaction. The compounds obtained after initial screening thus serve as "lead compounds" that can be developed further into potential drugs.

Pathogenic mycobacteria are the causative agents of a number of human and animal diseases. For example, tuberculosis is a health problem of considerable importance in the human population. Recent estimates are that as much as one-third of the population of the world is infected with *M. tuberculosis*, that there are 30 million active cases, that there are some 10 million new cases annually and that TB causes some 6 percent of all deaths worldwide (see e.g., Dye et al., 1999). Despite availability of chemotherapeutic agents, persistence and multi-drug resistance make it difficult to eliminate *M. tuberculosis* as a major health threat using currently available intervention strategies. It is known that *M. tuberculosis* survives within the hostile environment of macrophages and it is difficult to eliminate this form completely. Identification of new classes of drugs, which are active against latent TB, is thus considered imperative.

Development of novel drugs against TB has become a challenging area of research because of the unusual ability of the TB pathogen (*M. tuberculosis*) to resist drugs. Such resistance arises not only due to mutations but also due to the ability of the pathogen to enter into a dormant phase in which it can persist for prolonged periods of time (see e.g., Stewart et al., 2003). This happens particularly when it is encapsulated within a granuloma—a structure formed by the activated monocyte—macrophage system of the host. The conditions within the granuloma are far from ideal for mycobacterial growth. In particular, *M. tuberculosis* is an aerobic organism, whereas the conditions within the granuloma are highly anaerobic. Although under such conditions active growth is halted, the bacteria can persist indefinitely by entering into a dormant phase. Drug therapy further accelerates the shift from the active to the dormant or persistent phase (Coates et al., 2002). Treatment with the presently available drugs therefore can potentially cause the accumulation of dormant bacilli, which can reactivate themselves at a later stage. The dormant bacilli are therefore the major cause of concern as it leads to persistence of TB, which cannot be cured easily.

The persistent state can be mimicked under laboratory conditions by growing *M. tuberculosis* to stationary phase or growing the organism under hypoxic conditions or nutrient deprivation (Yuan et al., 1996; Sherman et al., 2001; Betts et al., 2002). It has been found that under these conditions the expression of a large number of genes are induced which are possibly required for the viability of the organism in the persistent phase. The proteins induced in the persistent phase can be considered as drug targets for preventing persistent TB. The 16 kDa alpha-crystallin like heat-shock protein, Hsp16.3 is an extremely important component of the dormant phase metabolism of the pathogen. It has also been demonstrated that over-expression of this protein in wild-type M. tuberculosis resulted in a slower decline in viability following the end of log-phase (Yuan et al., 1996). The protein has been demonstrated to be able to inhibit the thermal denaturation of various other proteins (Chang et al., 1996). From these evidences it has been suggested that the Hsp16.3 may play a role in enhancing long-term protein stability and therefore long-term survival in mycobacteria.

More recently the regulation of the *M. tuberculosis* hypoxic response has been elucidated. Under hypoxic conditions the expression of an operon encoding two polypeptides, which are constituents of a two-component signaling system (Rv3133c/3132c), is induced. Gene disruption experiments indicate that the induction of Hsp16.3 gene expression under hypoxic conditions is severely impaired (Sherman et al., 2001). This indicates that Hsp16.3 is a key player in the hypoxic response.

Hsp16.3 belongs to a family of proteins known as alpha-crystallin (Acr), which play an important role in the maintenance of the transparency of vertebrate eye. The primary function of these proteins is to act as molecular chaperons. Most of bacterial homologues of this protein have been found to play an important role in spore formation in *Bacillus subtilis* and are induced in response to acute stresses in other microorganisms. Initially the *M. tuberculosis* Acr (Hsp16.3) protein was characterized as a major membrane protein but subsequent work has revealed that it is a potent ATP-independent chaperon whose complex oligomeric active structure consists of trimer of trimers (Chang et al., 1996).

Hsp16.3 expression has also been found to be induced during the course of in vitro infection of macrophages. When the gene for Hsp16.3 (acr) of *M. tuberculosis* was replaced with a hygromycin cassette by allelic exchange in *M. tuberculosis* H37Rv, the resulting strain was shown to be equivalent to wild type H37Rv in in vitro growth rate and infectivity but was significantly impaired for growth in both mouse bone marrow derived macrophages and THP-1 cells (Yuan et al., 1998). These results indicate that Hsp16.3 plays an important role in maintenance of long-term viability during latent, asymptotic infections. That Hsp 16.3 is at least one of the key virulence factors has been clearly demonstrated by eliminating or down regulating the expression of the alpha-crystallin heat shock protein gene (acr) (Barry III et al., U.S. Pat. No. 6,403,100). As a result the virulent strain of *M. tuberculosis* became attenuated, which means that it lost its virulence substantially, indicating that Hsp16.3 is one of the key players of mycobacterial virulence. Given this background it is clear that the effective inhibitors against the Hsp16.3 protein would be of significant importance to combat persistent TB.

Peptides are considered as useful therapeutic agents as they can specifically interfere with protein-protein interaction. Nature abounds in various antimicrobial peptides (see e.g., the data base ANTIMIC: http://research.i2r.a-star.edu.sq/Templar/DB/ANTIMIC/). Some of these such as defensins act by interacting at the level of membrane permeabilization. However there are others like pyrrhocoricin (Otvos et al., 2000), which have specific cellular targets such as Hsp70 or DnaK, which like Hsp16.3, is a chaperon. Pyrrhocoricin specifically inhibits DnaK from bacterial sources such as *E. coli* but not human and hence examples such as this indicate that although chaperons are conserved in evolution there exists peptide binding pockets specifically present in bacterial chaperons, which can be targeted for drug design. Since naturally occurring peptide inhibitors of Hsp16.3 are as yet not known hence an alternative strategy of identifying peptide inhibitors through selection from a pool of phage displayed peptides has been developed as claimed in this disclosure.

OBJECTS OF THE INVENTION

The main object of the present invention provides peptide antagonists for inhibiting chaperone activity of Heat shock protein 16.3 (Hsp 16.3), a virulence factor necessary for survival of *Mycobacterium tuberculosis*.

Another object of the present invention relates to the process of identifying peptide antagonists inhibiting chaperone activity of Heat shock protein 16.3 (Hsp 16.3), a virulence factor necessary for survival of *Mycobacterium tuberculosis*.

Yet another process of the present invention relates to the use of the peptides for inhibiting chaperone activity of Heat shock protein 16.3 (Hsp 16.3), a virulence factor necessary for survival of *Mycobacterium tuberculosis*.

Yet another object of the present invention relates to the inhibition of chaperonic activity of Heat shock protein 16.3 (Hsp 16.3), mycobacterial virulence factor by the peptides.

Still another object of the present invention relates to the process of preparing the peptide antagonists of mycobacterial virulence factor.

BRIEF DESCRIPTION OF ACCOMPANYING FIGS

FIG. 1. Reverse phage ELISA to confirm the binding of phage clones displaying peptide sequences, Seq ID 9 and 21 to Hsp16.3. Selected phage clones displaying peptide sequences Seq ID 9 and 21 were amplified, concentrated through PEG precipitation reacted with Hsp 16.3 coated on the wells of a micro-titer plate. Unbound phages were removed by washing with TBST (0.5% Tween-20), and bound phage were detected with HRP-conjugated anti-M13 monoclonal antibody (1:1000) and ABTS substrate. Color development was monitored spectrophotometrically at 405 nm. The bar graph shows binding activity of phage clones displaying Seq ID 9 (white bar) and Seq ID 21 (black bar) to Hsp16.3 and BSA (background binding) as detected by reverse phage ELISA. The binding of same phage clones to Hsp 16.3 was found to be about three-fold higher as compared to non-specific control BSA.

FIG. 2. An example of dose dependent inhibition of chaperon activity of Hsp 16.3 by peptide of Seq ID 10 to support the claim that the peptides inhibit the activity of Hsp16.3. Aggregation assays were performed by heating 5 μM Alcohol dehydrogenase (ADH) to 50° C. directly in a spectrophotometer using a thermostated cuvette holder in a total reaction volume of 500 μl. Optical density was monitored at 360 nm for 1200 seconds and readings were taken at every 100 seconds interval. The ability of Hsp 16.3 to suppress aggregation (chaperon activity) was demonstrated by mixing ADH with Hsp 16.3 at a molar ratio of 5:4. Then the same experiment was performed in the presence of increasing concentrations of the Hsp16.3 binding peptide Seq IDs 10. Aggregation of ADH in the absence of Hsp 16.3 (black triangle). Aggregation in the presence of Hsp 16.3 (black circle). The same experiment when performed in the presence of increasing concentrations of the Hsp 16.3 binding peptide (Seq ID 10) 25 μM (white square), 50 μM (black square), 100 μM (white triangle). Only peptide control (ADH+100 μM peptide) (white circle). The similar results were obtained with Seq ID 22.

FIG. 3. An example to show the specificity of the inhibitory peptides for Hsp16.3 and not for alphaB-crystallin—a component of human eye lens. A similar assay as described in FIG. 2 was performed using alphaB-crystalline instead of Hsp16.3. The molar ratio between ADH and alphaB-crystallin was maintained 5:4 as in the case of Hsp 16.3. Aggregation in the absence of alphaB-crystallin (black triangle). Aggregation in the presence of alphaB-crystalline (black circle). The same experiment was performed in the presence of increasing concentrations of the Hsp16.3 binding peptide (Seq ID 10) 25 µM (white square), 50 µM (black square), 100 µM (white triangle). Only peptide control (ADH+100 µM peptide) (white circle). The similar results were obtained with Seq ID 22.

Figure 4:
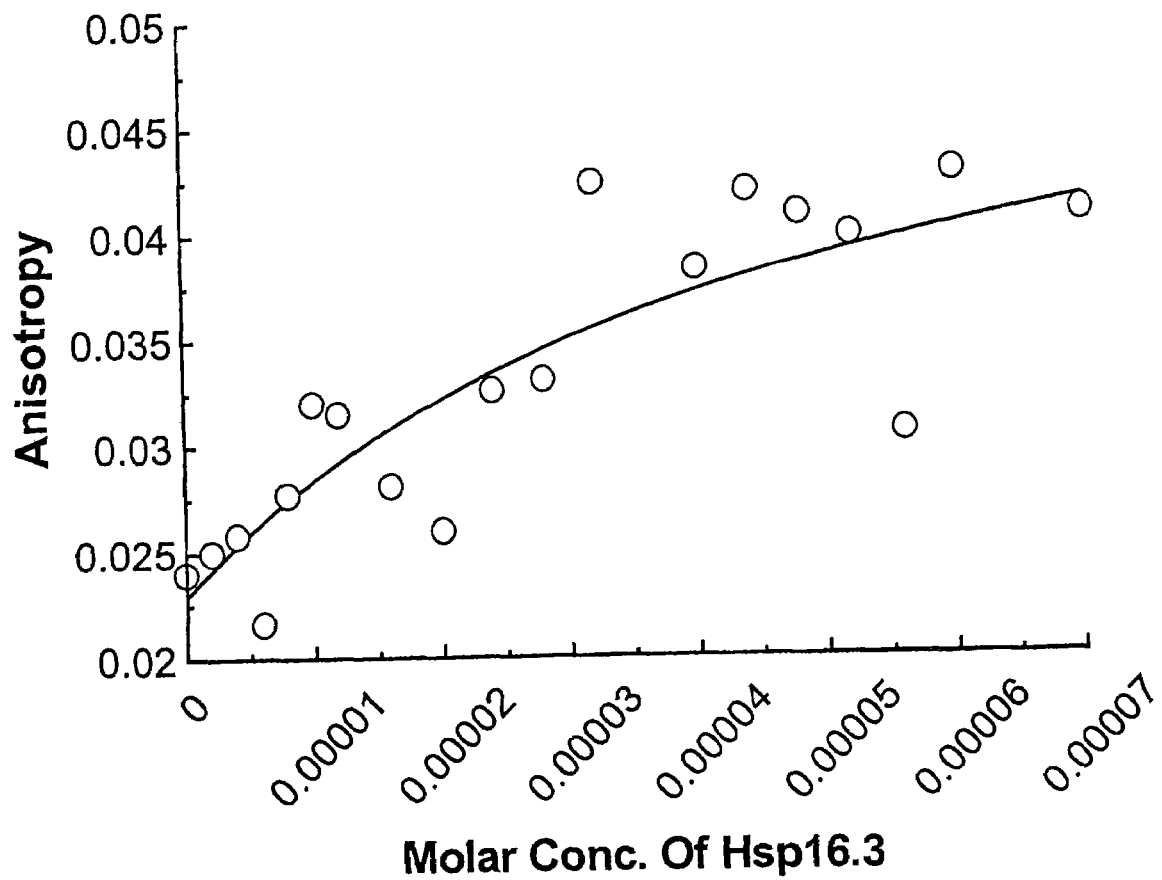

FIG. 4. Determination of affinity constant by using fluorescence anisotropy. Titration of fluoresceinated peptide (Seq ID 22) at a concentration of 200 nM with increasing concentrations of Hsp 16.3. The line shown is the best fit to a single-site binding equation. Each point is an average of three independent measurements. The solution conditions were 50 mM sodium phosphate buffer, pH 7.5, containing 300 mM NaCl. The temperature was 25 ± 1° C. Excitation and emission wavelengths were 495 and 520 nm, respectively. By this technique the $K_d$ value of Seq ID 22 for Hsp16.3 was determined to be ~40 µM. In the same way the $K_d$ value of Seq ID 10 for Hsp16.3 to be ~50 µM.

Figure 5A:
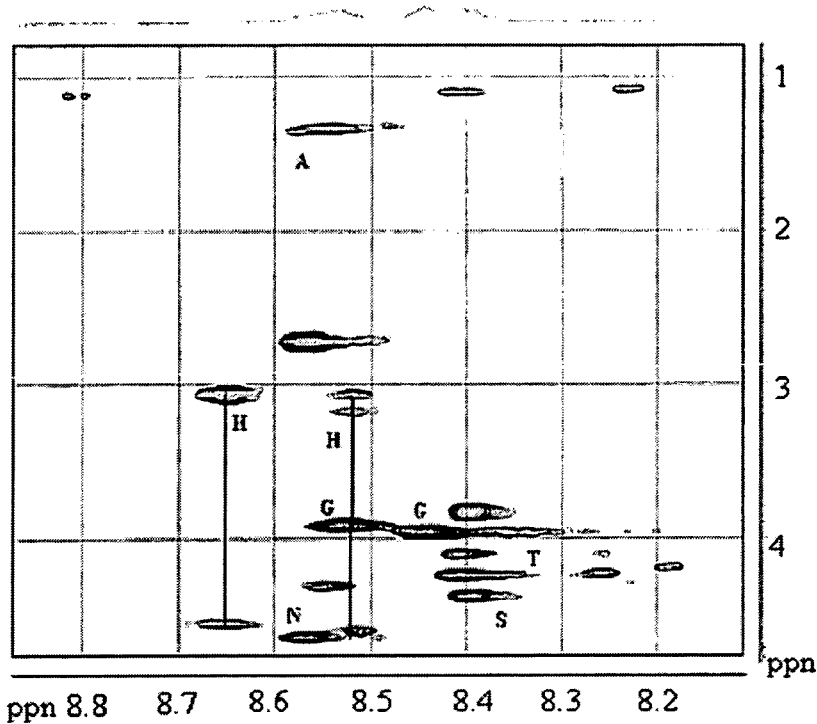
Figure 5:
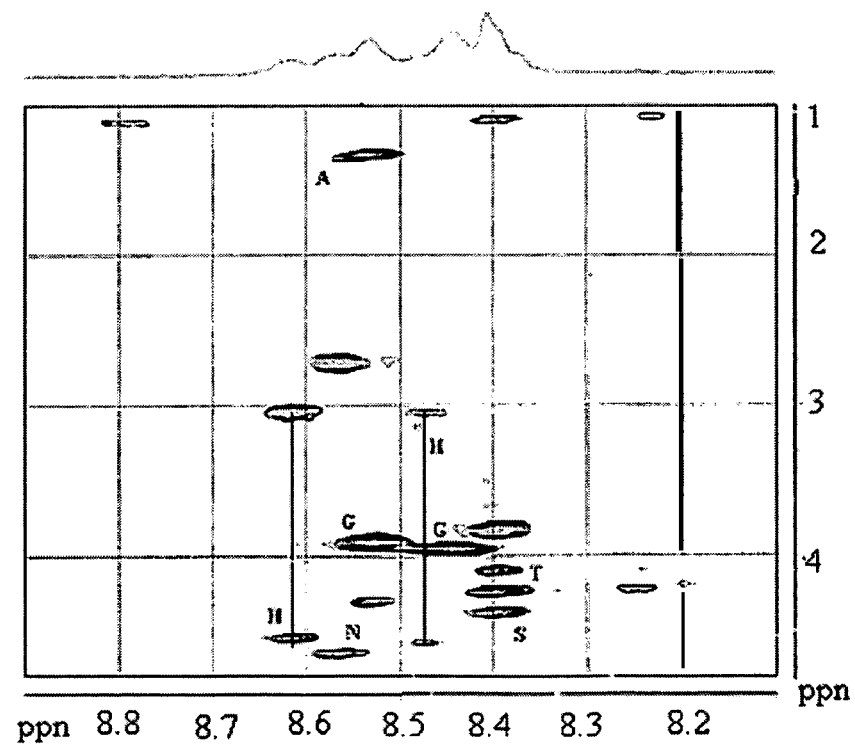

FIG. 5. Comparison of chemical shifts of amide protons of free peptide (Seq ID 10) (a) and peptide with Hsp16.3 protein (b). Resonance assignments are indicated with a one-letter amino acid code. All NMR spectra were taken in a Bruker DRX-500 spectrometer equipped with a Z-field gradient probe. All measurements were done in high precision 5-mm NMR tubes in 20 mM sodium phosphate buffer, pH 7.0, containing 250 mM NaCl in 90% $H_2O$ and 10% $D_2O$ at 4° C. TOCSY spectra were measured using standard pulse sequences in the Bruker pulse library using WATERGATE water suppression method. Standard Bruker software (Xwin-NMR version 1.3) was used to acquire and process the NMR data. The NMR samples were adjusted to a protein concentration of 0.1 mM and a 20-fold ligand excess (2 mM) over binding sites was used throughout the studies. A significant chemical shift occurs in both histidines denoted as H residues.

SUMMARY OF THE INVENTION

The invention describes a method to generate peptide inhibitors of a mycobacterial virulence factor Hsp16.3, which is involved in promoting persistence—a major cause of concern in TB therapy and a method to assay in vitro the inhibitory effect of inhibitors of the Hsp16.3 including peptide inhibitors generated by the method developed by the inventors.

The invention describes two peptides which inhibit the chaperon activity of Hsp16.3. The peptides are important not only for their ability to inhibit the activity of Hsp16.3 but also to derive structural information leading to rational drug design. In other words these peptides can serve as lead compounds for future development of anti-TB formulations that target Hsp16.3.

The invention is particularly important since by the method of invention it is possible to obtain inhibitors that are specific for Hsp16.3 that do not inhibit other related proteins present in the host for example alphaB-crystallin, a component of human eye lens.

DETAIL DESCRIPTION OF THE INVENTION

The progression of *M. tuberculosis*, the causative agent of TB, from the actively growing state to a dormant state is a major problem in TB therapy as it results in a persistent disease that is difficult to cure. This invention relates to the dormancy promoting protein Hsp16.3 of *M. tuberculosis* and developing peptide inhibitors against it.

The target gene (acr) for Hsp16.3, alpha-crystallin like heat shock protein of *M. tuberculosis* is known and its sequence is a matter of public knowledge. The acr gene was first published in 1992 by two groups (Verbon et al., 1992; Lee et al., 1992.). The 14,000-molecular-weight antigen of *M. tuberculosis* is related to the alpha-crystallin family of low-molecular weight heat shock proteins. The amino acid and nucleic acid sequences are published in GenBank and have the following GenBank Accession Numbers S79751 and M76712. The protein Hsp 16.3 was obtained from the *E. coli* strain EC-16. This strain harbors a recombinant plasmid comprising of the acr CDS (Seq ID 23), cloned in the *E. coli* expression vector pQE-8, a commercially available vector, that can be obtained from Qiagen Inc. Stanford, USA. EC-16 cells can be induced to express high levels of Hsp 16.3 (Seq ID 24) by the addition of isopropyl-1thio-D-galactopyranoside (IPTG) in the culture medium. The strain EC-16 was obtained on the basis of a material transfer agreement with the Medical Research Council (henceforth referred to as MRC) of London. Due permission has been sought from Dr. Juraj Ivanyi who originally developed this clone and the representative of the MRC for using this expression vector to produce Hsp 16.3 to be used for identifying inhibitors against this protein. The use of this vector is merely a matter of convenience and ready availability and simply to avoid redundancy of constructs; as otherwise the inventors themselves are familiar with the art of amplifying the aforesaid CDS by polymerase chain reaction (PCR) from the DNA of *M. tuberculosis* H37Rv, and cloning of acr in various commercially available expression vectors of choice. The protein is expressed from the recombinant plasmid as a fusion protein with a stretch of 6×His residues at the N-terminal end. This His-tagged protein can be purified using affinity chromatography on a $Ni^{2+}$-NTA column purchased from Qiagen Inc. Stanford, USA.

As a part of this disclosure, screening of phage display libraries has been used to identify peptide sequences that bind to Hsp16.3. Phage display is an in vitro screening technique in which peptides are genetically fused to a coat protein of a bacteriophage, resulting in display of the fused protein on the exterior of the phage virion. This physical linkage between the displayed protein and the DNA encoding it allows screening of vast number of variants, each linked to its original corresponding DNA sequence, by a simple panning process called 'biopanning'. In its simplest form biopanning is carried out by incubating the pool of phage-displayed variants on the immobilized target. The biopanning procedure is carried out for several rounds and after each round phage displaying peptide(s) having the capability to bind to the protein are enriched to such an extent that it is possible to identify a definite pattern in the amino acid sequence of the peptides bound to the target. Successful phage display is achieved when a unique peptide sequence or at least a consensus sequence is derived after successive rounds of panning. Although the broad outlines for screening have been suggested by the manufacturers of phage display kits, each target has its own peculiarities which requires careful application of binding techniques and elution conditions so that a meaningful peptide consensus emerges which can be subsequently synthesized and checked for binding activity. The success of the procedure depends on various factors. Globular proteins like bovine serum albumin (BSA) do not have specific ligand binding pockets and thus in such cases panning procedures do not lead to discernible enrichment, but on the other hand proteins like antibodies which have defined ligand binding sites are known to bind specific peptides efficiently. As a part of this disclosure it is shown that after repeated rounds of panning on Hsp16.3 enriched phage displayed peptide sequences can be identified and so it follows that Hsp16.3 has ligand binding sites which can be targeted to develop peptide inhibitors.

Phage display libraries such as the heptapeptide (Ph.D.-7) and dodecapeptide (Ph.D.-12) displaying phage are commercially available from New England Biolabs, Inc. (Beverly, Mass., USA). Hsp16.3 protein can be obtained as a 6×His tagged protein from recombinant *E. coli* strains such as EC-16. Similar constructs can be easily made by PCR amplifying the acr gene from *M. tuberculosis* H37Rv DNA and incorporating it into any expression vector which has the provision to allow purification using an affinity tag either 6×His or any other affinity tag. Strain H37Rv is typical of the pathogenic forms of *M. tuberculosis*. Qualified individuals can obtain DNA made from this strain from Colorado State University, Fort Collins under the NIH, NIAID Contract NO1-AI-75320 entitled "*Tuberculosis* Research Materials and Vaccine Testing Contract" (administered by Dr. Ann Ginsberg, *Tuberculosis* Program Officer, NIAID, Solar Building, Room 3A31, Bethesda Md. 20892). The target protein after purification by affinity chromatography is immobilized on 96-well microtiter plate (Tarson, Mumbai, India) after incubating overnight in bicarbonate buffer at 4° C. After the excess protein is removed, a phage display library such as Ph.D.-7 is added and incubated for 30-60 min. After removing excess phage the bound phage are eluted with 100 µl elution buffer (0.2 M Glycine-HCl, pH 2.2 containing 1 mg/mL BSA) and neutralized with 15 µl 1 M Tris HCl, pH 9.1. The process is repeated for several rounds until a consensus sequence is derived. The elution conditions are also important. Incorporation of Tween-20 in the wash buffer ensures that superfluous binding is minimized. As a part of this disclosure it is shown that three rounds of biopanning accompanied by washing in the presence of increasing concentrations of Tween-20 at each step gives best results in the context of Hsp16.3. Following the initial screening, potential target binding phage can be further screened using the technique of reverse phage ELISA in which phage are allowed to bind to target coated on microtiter plates and the binding is monitored by using horseradish peroxidase (HRP)-conjugated anti-M13 monoclonal antibody (Amersham Pharmacia Biotech, Uppsala, Sweden).

In a phage display library the peptides are expressed fused with coat proteins. Screening of phage display libraries can give important information about the sequence of peptides having potential target binding activity. However for actual proof of binding, it is necessary to synthesize the peptide chemically and demonstrate its binding using biophysical techniques. In order to synthesize a peptide it is important to remember that while it is a part of the coat protein its conformational activities are influenced not only by its own amino acid sequence but also the flanking sequences. Hence in the art of phage display technique it is mandatory to incorporate the spacer sequence Gly-Gly-Gly-Ser at the C-terminal. Chemically synthesized peptides therefore must incorporate this sequence and also the C-terminal must be amidated. Once a desired peptide is synthesized its binding needs to be demonstrated. Fluorescence anisotropy can be used as an important method to obtain an idea about interaction efficiencies between Hsp16.3 and the binding peptide. Such method depends on the principle that when a fluorescent molecule is excited with plane polarized light; light is emitted in the same polarized plane, provided that the molecule remains stationary throughout the excited state (which has a duration of 4 nanoseconds for fluorescein). If the molecule rotates and tumbles out of this plane during the excited state, light is emitted in a different plane from the excitation light. If vertically polarized light is exciting the fluorophore, the intensity of the emitted light can be monitored in vertical and horizontal planes (degree of movement of emission intensity from vertical to horizontal plane is related to the mobility of the fluorescent labeled molecule). If a molecule is very large, little movement occurs during excitation and the emitted light remains highly polarized. If a molecule is small, rotation and tumbling is faster and the emitted light is depolarized relative to the excitation plane. If the same molecule is bound to protein the tumbling slows down and as a result fluorescence polarization or anisotropy increases. A part of this disclosure is the process of determination of binding affinity of these peptides to Hsp16.3 by conjugating the peptide with fluorescein isothiocyanate (FITC), purchased from Molecular Probes Inc. (Eugene, Oreg.) and determining binding constant by measuring increase in fluorescence anisotropy upon the addition of the Hsp16.3 to the fluorescein conjugated peptide.

The binding of a peptide need not necessarily result in inhibition. Inhibition will happen only if binding leads to significant changes in the active site. It is therefore necessary to demonstrate that the peptides are capable of inhibiting the activity of the Hsp 16.3 protein. A part of the invention is the development of a peptide inhibition assay for Hsp16.3. The method is based on aggregation based assays. The standard assay used for assaying the activity of alpha-crystallin like proteins is to study the protection it confers against heat induced aggregation of proteins, the aggregation activity being measured spectrophotometrically. Yeast alcohol dehydrogenase (ADH), purchased from Sisco Research Laboratory, Mumbai, India, is used for aggregation studies. Aggregation of 5 µM ADH at 50° C. can be measured as an apparent optical density at 360 nm using a spectrophotometer equipped with a thermostated cuvette holder in a total reaction volume of 500 µl. The chaperon activity of Hsp16.3 can be determined by mixing ADH with Hsp16.3 at a molar ratio of 5:4 which is equivalent to a ratio of about 12:1 between ADH and Hsp16.3 assuming a nonameric structure of Hsp16.3 as the functional unit (Chang et al., 1996) and aggregation rates again determined spectrophotometrically. Then the same experiment can be repeated in the presence of increasing concentrations of peptide inhibitors.

An important aspect of inhibitor development procedures is to understand the nature of interactions between the inhibitor and its target. Nuclear Magnetic Resonance or NMR as scientists abbreviate it, is a phenomenon which occurs when the nuclei of certain atoms are immersed in a static magnetic field and exposed to a second oscillating magnetic field. Some nuclei experience this phenomenon, and others do not, depending upon whether they possess a property called spin. NMR spectroscopy is the use of the NMR phenomenon to study physical, chemical, and biological properties of matter. As a consequence, NMR spectroscopy finds applications in several areas of science. NMR spectroscopy is routinely used by chemists to study chemical structure using one-dimensional and two-dimensional techniques. NMR spectroscopy can solve protein and peptide structures in solution, thus protein structure and dynamics under physiological conditions can be investigated. As a part of this disclosure it is shown that histidine residues in one of the two peptide inhibitors namely Seq ID 10 interact with Hsp16.3 as determined by NMR.

Accordingly, the present invention relates to a peptide antagonists having SEQ ID No. 10 and SEQ ID No. 22 for inhibiting chaperone activity of Heat shock protein 16.3 (Hsp 16.3), a virulence factor necessary for survival of *Mycobacterium tuberculosis*.

Another embodiment of the present invention relates to a method of inhibiting chaperone activity of Heat shock protein 16.3 (Hsp 16.3), a virulence factor necessary for survival of *Mycobacterium tuberculosis*, wherein said method comprises inhibiting the chaperone activity of Hsp 16.3 protein by antagonist peptides having SEQ ID 10 and SEQ ID 22.

Another embodiment of the present invention relates to a method of preparing peptide antagonists having SEQ ID No. 10 and SEQ ID No. 22, for inhibiting activity of chaperone activity of heat shock protein 16.3 (Hsp 16.3), a virulence factor necessary for survival of *Mycobacterium tuberculosis*, said method comprising steps of:
(a) biopanning phage display library 7 (Ph.D-7) and phage display library (Ph.D-12),
(b) selecting 8 clones from each of the Ph.D-7 and Ph.D 12,
(c) identifying SEQ ID 9 and SEQ ID 21, as the sequences having high binding affinity to target protein Hsp 16.3, (d) synthesizing SEQ ID 9 and SEQ ID 21 commercially to add mandatory sequence Gly-Gly-Gly-Ser at the C-terminal to obtain peptides having SEQ ID No. 10 and SEQ ID No. 22 using convention solid state method, and (e) studying the antagonist activity of SEQ ID No. 10 and SEQ ID No. 22.

Another embodiment of the present invention relates to the Peptides said peptides are very specific to Hsp16.3 mycobacterial protein.

Still another embodiment of the present invention relates to the Peptides wherein Kd value of peptide having SEQ ID No. 10 is 50 µM and peptide having SEQ ID No. 22 is 40 µM.

Yet another embodiment to the present invention relates to the Peptides wherein 47 µM of peptide having SEQ ID No. 10 and 57 µM of peptide having SEQ ID No. 22 inhibits 50% of chaperonic activity of Hsp 16.3 factor.

One more embodiment of the present invention relates to the Peptides wherein said peptides in the range of about 90 to 110 µM completely inhibits the chaperone activity of Hsp 16.3 protein.

Another embodiment of the present invention relates to the Peptides wherein said peptides of about 100 µM completely inhibit the chaperone activity of Hsp 16.3 protein.

Figure 3A:
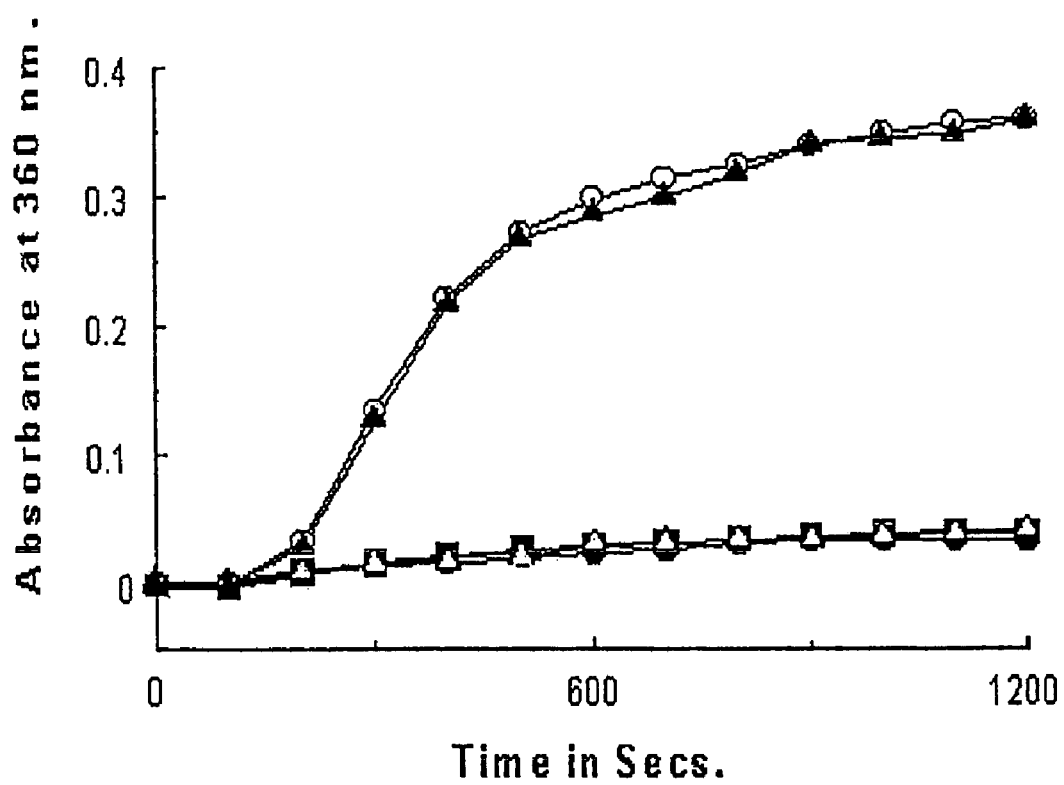
Figure 3B:
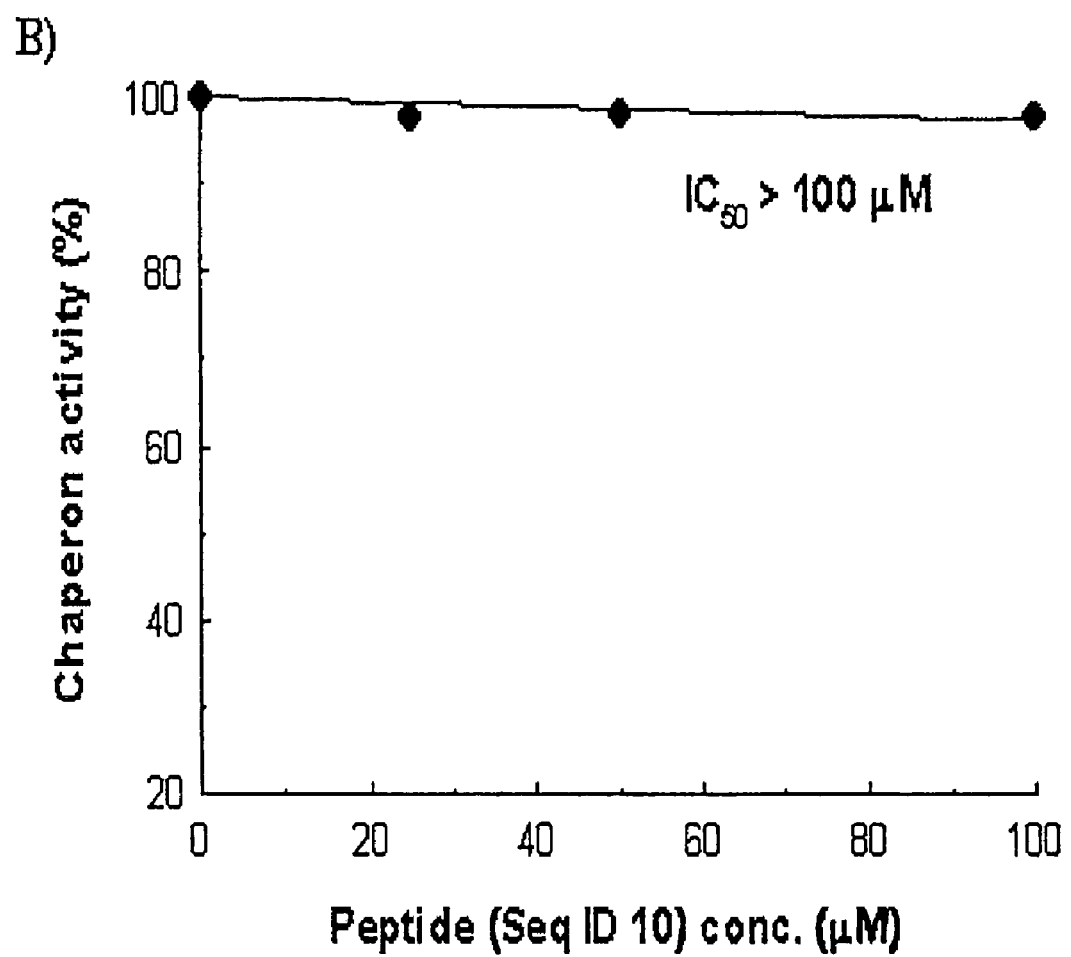

Still another embodiment of the present invention relates to the Peptides wherein said peptides are very specific to chaperonic protein of Hsp16.3 and does not inhibit any other chaperone protein (FIGS. 3A and 3B).

One more embodiment of the present invention relates to the Peptides wherein said peptides reduce chaperone activity of Hsp 16.3 by about 90% in the presence of the peptides.

The invention is illustrated by the following examples wherein the following examples are given by the way of illustration of the present invention and should not be construed to limit the scope of the present invention.

EXAMPLES

Example 1

Phage display libraries such as the heptapeptide (Ph.D.-7) and dodecapeptide (Ph.D.-12) displaying phage are commercially available from New England Biolabs, Inc. (Beverly, Mass., USA). Hsp16.3 protein can be obtained as a 6×His tagged protein from recombinant E. coli strains such as EC-16. Similar constructs can be easily made by PCR amplifying the acr gene from M. tuberculosis H37Rv DNA and incorporating it into any expression vector which has the provision to allow purification using an affinity tag either 6×His or any other affinity tag. Strain H37Rv is typical of the pathogenic forms of M. tuberculosis. Qualified individuals can obtain DNA made from this strain from Colorado State University, Fort Collins under the NIH, NIAID Contract NO1-AI-75320 entitled "Tuberculosis Research Materials and Vaccine Testing Contract" (administered by Dr. Ann Ginsberg, Tuberculosis Program Officer, NIAID, Solar Building, Room 3A31, Bethesda Md. 20892). The target protein after purification by affinity chromatography is immobilized on 96-well microtiter plate (Tarson, Mumbai, India) after incubating overnight in bicarbonate buffer at 4° C. After the excess protein is removed, a phage display library such as Ph.D.-7 is added and incubated for 30-60 min. After removing excess phage the bound phage are eluted with 100 μl elution buffer (0.2 M Glycine-HCl, pH 2.2 containing 1 mg/mL BSA) and neutralized with 15 μl 1 M Tris HCl, pH 9.1. The process is repeated for several rounds until a consensus sequence is derived. The elution conditions are also important. Incorporation of Tween-20 in the wash buffer ensures that superfluous binding is minimized. As a part of this disclosure it is shown that three rounds of biopanning accompanied by washing in the presence of increasing concentrations of Tween-20 at each step gives best results in the context of Hsp16.3. Following the initial screening, potential target binding phage can be further screened using the technique of reverse phage ELISA in which phage are allowed to bind to target coated on microtiter plates and the binding is monitored by using horseradish peroxidase (HRP)-conjugated anti-M13 monoclonal antibody (Amersham Pharmacia Biotech, Uppsala, Sweden).

Biological Enrichment of Phage Displaying Specific Peptide Sequences Through Biopanning on Hsp16.3 Target:

After the third round of panning of Ph.D.-7 library on Hsp16.3, it was found that out of the eight randomly selected phage clones (Seq ID 1-8), which were sequenced for the peptide-coding region, five were identical. Seq ID 9 represents the consensus sequence (Lys-Met-His-Ala-Thr-Asn-His), which indicates that this peptide sequence has relatively high affinity for binding to the target protein. In the case of Ph.D.-12 library the results were more striking. Out of the ten clones sequenced after third panning, nine clones (Seq ID 11-20) were identical and the consensus peptide sequence (Seq ID 21) in this case was Tyr-Pro-His-His-Phe-Lys-His-Arg-His-Ile-Pro-Ile. The binding of phage clones displaying peptides (Seq IDs 9 and 21) was confirmed further by performing a reverse phage ELISA. The binding of these phage clones to Hsp16.3 was found to be about three-fold higher as compared to background binding (Tables 1 and 2). Screening of phage display libraries to identify Hsp16.3 binding peptide sequences. The wells of a micro-titer plate were coated with Hsp16.3 in 0.1 M $NaHCO_3$ buffer, pH 8.6 and phage display libraries Ph.D.-7 or Ph.D.-12 were added. Non-binding phage were washed off with TBS containing 0.1% [v/v] Tween-20. Phage bound to the Hsp16.3 protein were eluted with 0.2 M Glycine—HCl buffer (pH 2.2), containing 1 mg/ml BSA. The eluted phage were then amplified on *E. coli* ER2738 host strain, purified and concentrated by PEG precipitation and used in the next round of bio-panning. For successive rounds of bio-panning the concentration of Tween-20 in wash buffer was raised from 0.1% to 0.3% (second round) and 0.5% (third round). After three rounds of positive selection, individual plaques were picked at random, amplified and single stranded-phage DNA was isolated for sequencing. Table 1 shows phage displayed peptide sequences (Seq ID 1-8) identified after the third round of bio-panning with the Ph.D.7 library. The sequence that is most frequently encountered in this group is designated as Seq ID 9. Seq ID 10 represents the sequence of a synthetic peptide obtained after adding the mandatory Gly-Gly-Gly-Ser linker at the C-terminal end of Seq ID 9. Similarly Table 2 shows the peptide sequences (Seq ID 11-20) obtained after the third round of bio-panning with the Ph.D.12 library. Seq ID 21 represents the most frequently occurring sequence within this group. Seq ID 22 represents the sequence of the synthetic peptide obtained after adding the mandatory Gly-Gly-Gly-Ser linker at the C-terminal end of Seq ID 21.

TABLE 1

Biopanning of Ph.D.-7

| Seq ID no. | Amino acid sequence | | | | | | | | | |
|---|---|---|---|---|---|---|---|---|---|---|
| 1. | Gly | Val | Glu | Asn | Val | Ser | Trp | | | |
| 2. | Lys | Met | His | Ala | Thr | Asn | His | | | |
| 3. | Lys | Met | His | Ala | Thr | Asn | His | | | |
| 4. | Lys | Met | His | Ala | Thr | Asn | His | | | |
| 5. | Leu | Pro | Ala | Lys | Asn | Phe | His | | | |
| 6. | Phe | Pro | Pro | Leu | Lys | Ser | Pro | | | |
| 7. | Lys | Met | His | Ala | Thr | Asn | His | | | |
| 8. | Lys | Met | His | Ala | Thr | Asn | His | | | |
| 9. | Lys | Met | His | Ala | Thr | Asn | His | | | |
| 10. | Lys | Met | His | Ala | Thr | Asn | His | Gly | Gly | Gly | Ser |

TABLE 2

Biopanning of Ph.D.-12

| Seq ID no. | Amino acid sequence | | | | | | | | | | | | | | | |
|---|---|---|---|---|---|---|---|---|---|---|---|---|---|---|---|---|
| 11. | Tyr | Pro | His | His | Phe | Lys | His | Arg | His | Ile | Pro | Ile | | | | |
| 12. | Tyr | Pro | His | His | Phe | Lys | His | Arg | His | Ile | Pro | Ile | | | | |
| 13. | Tyr | Pro | His | His | Phe | Lys | His | Arg | His | Ile | Pro | Ile | | | | |
| 14. | Tyr | Pro | His | His | Phe | Lys | His | Arg | His | Ile | Pro | Ile | | | | |
| 15. | Tyr | Pro | His | His | Phe | Lys | His | Arg | His | Ile | Pro | Ile | | | | |
| 16. | Ala | Tyr | Lys | Pro | Ile | Ala | His | Phe | Ile | Ser | Pro | Ala | | | | |
| 17. | Tyr | Pro | His | His | Phe | Lys | His | Arg | His | Ile | Pro | Ile | | | | |
| 18. | Tyr | Pro | His | His | Phe | Lys | His | Arg | His | Ile | Pro | Ile | | | | |
| 19. | Tyr | Pro | His | His | Phe | Lys | His | Arg | His | Ile | Pro | Ile | | | | |
| 20. | Tyr | Pro | His | His | Phe | Lys | His | Arg | His | Ile | Pro | Ile | | | | |
| 21. | Tyr | Pro | His | His | Phe | Lys | His | Arg | His | Ile | Pro | Ile | | | | |
| 22 | Tyr | Pro | His | His | Phe | Lys | His | Arg | His | Ile | Pro | Ile | Gly | Gly | Gly | Ser |

Example 2
Synthesis, Labeling and Purification of Peptides:

The peptides (Seq ID 10 and Seq ID 22) were produced on a 0.12 mmole scale using a Biolynx 4175-peptide synthesizer. They were synthesized by the solid-phase method with the standard 9-flurenylmethoxycarbonyl (Fmoc) chemistry. The peptides were synthesized with their C-terminus amidated using MBHA-Rink amide resin (Novabiochem, San Diego, Calif.). Amino acids (Novabiochem, San Diego, Calif.) except those stated below, were used as N-terminal Fmoc protected and C-terminally pentafluorophenyl ester activated with N-hydroxybenzotriazole (HOBT) (Novabiochem, San Diego, Calif.). Thr, His, Arg, Ile, Ser, Ala and Pro were used in the COOH form using benzotriazole-1-yloxytripyrrolidinophosphoriumhexafluorophosphate (PyBop) (Novabiochem, San Diego, Calif.) as activating agent with HOBT and N,N-diisopropylethylamine (DIPEA) (Fluka chemie, GmbH.) (1:1:2). The Fmoc protecting group was removed from the N-terminus of the peptide resin by 20% piperidine in dimethylformamide (DMF) (Merck, Germany) followed by washes with DMF. The resin was dried under vacuum. The peptides were cleaved using standard trifluoroacetic acid (TFA) (Spectrochem, Mumbai, India) cleavage procedures followed by multiple ether extractions. Both the peptides were purified by reverse phase HPLC on C-4 column (Vydac, Hesperin, Calif.) using 0-100% acetonitrile in 0.1% TFA and characterized by NMR. Both the peptides were labeled with FITC while still on the resin, thus placing the fluorophore on the N-terminus of the peptide. One equivalent of dried resin in 2% piperidine in DMF was mixed with 30 equivalent of FITC and 10 equivalent of DIPEA in a microcentrifuge tube and the reaction was allowed to proceed for 2-3 hours at room temperature with occasional mixing. Following several washes with DMF, t-Amyl alcohol, glacial acetic acid and diethyl ether, the resin was dried under vacuum. The dye conjugated peptides were cleaved from the resin, and the side-chain protecting groups were removed by incubating in reagent K (TFA:phenol:thioanisole:water:ethanedithiol:: 82.5:5:5:5:2.5) for 3 h at room temperature. The peptides were purified as mentioned earlier. The sequence that is most frequently encountered in this group is designated as Seq ID 9. Seq ID 10 represents the sequence of a synthetic peptide obtained after adding the mandatory Gly-Gly-Gly-Ser linker at the C-terminal end of Seq ID 9. Similarly Table 2 shows the peptide sequences (Seq ID 11-20) obtained after the third round of bio-panning with the Ph.D. 12 library. Seq ID 21 represents the most frequently occurring sequence within this group. Seq ID 22 represents the sequence of the synthetic peptide obtained after adding the mandatory Gly-Gly-Gly-Ser linker at the C-terminal end of Seq ID 21.

Example 3
Reverse Phage ELISA:

A reverse phage ELISA was used to evaluate the ability of individual phage clones to bind to Hsp16.3. Briefly; 30 μg/well of Hsp16.3 in 0.1 M NaHCO$_3$ buffer, pH 8.6, was added to a 96-well microtiter plate and blocked with 2% skimmed milk powder in TBS. BSA (30 μg/well) and TBS were used as negative and blank controls respectively. The selected peptide phage clones, amplified and concentrated with PEG-NaCl precipitation method, were added to each coated well ($1 \times 10^7$ to $1 \times 10^8$ pfus/well), and incubated for 2 hours at room temperature. Unbound phage were removed by washing with TBST (0.5% Tween-20), and bound phage were detected with HRP-conjugated anti-M13 monoclonal antibody (1:1000) and 2,2'-azino-bis(3-ethylbenzothiazoline-6-sulfonic acid) (ABTS) substrate (Roche, Mannheim, Germany). Plates were read at A$_{405}$. If the phage clones obtained after screening are true Hsp16.3 binders then ELISA signals substantially higher than the background are obtained. By this technique it was confirmed that the phages clones picked up after third round of screening bind to Hsp16.3 (FIG. 1). The bar graph shows binding activity of phage clones displaying Seq ID 9 (white bar) and Seq ID 21 (black bar) to Hsp16.3 and BSA (background binding) as detected by reverse phage ELISA. The binding of same phage clones to Hsp16.3 was found to be about three-fold higher as compared to non-specific control, BSA. The results confirm that the selected phage clones bind specifically to the chosen target—the Hsp16.3 protein, and not to a non-specific target such as BSA. Hence the peptides displayed on these phage clones truly represent Hsp16.3 binding peptide sequences.

Example 4

Figure 2A:
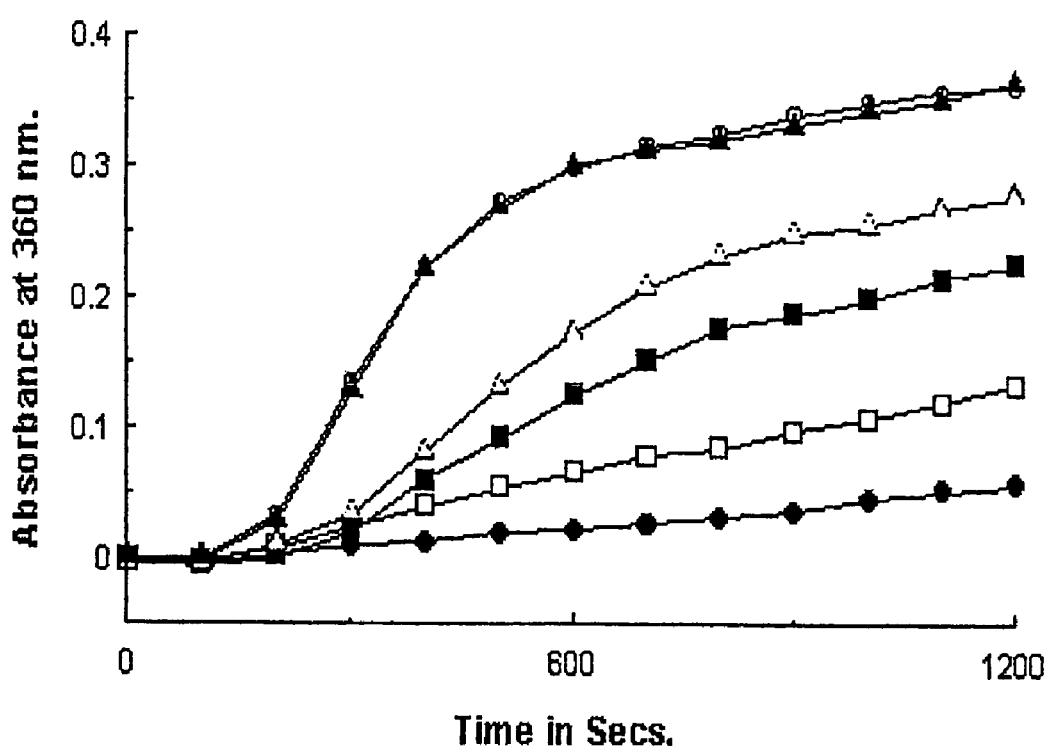

In Vitro Assay for Anti Hsp16.3 Activity:

A part of the invention is the peptide inhibition assay for Hsp16.3 comprising of heat treating ADH alone, ADH+Hsp16.3 and ADH+Hsp16.3+25, 50 and 100 µM peptide. When ADH is heated it aggregates and there is an increase of optical density. In the presence of Hsp16.3 aggregation is prevented, but in the presence of peptide aggregation is again observed if Hsp16.3 activity is inhibited. Aggregation of 5 µM ADH at 50° C. was measured as an apparent optical density at 360 nm using Hitachi spectrophotometer equipped with a thermostated cuvette holder in a total reaction volume of 500 µl. The chaperon activity of Hsp16.3 was determined by mixing ADH with Hsp16.3 at a molar ratio of 5:4 and aggregation rates were again determined spectrophotometrically. Then the same experiment was performed in the presence of increasing concentrations of the Hsp16.3 binding peptides (Seq IDs 10 and 22) (FIG. 2).

An example of dose dependent inhibition of chaperon activity of Hsp16.3 by peptide of Seq ID 10 to support the claim that the peptides inhibit the activity of Hsp16.3. Aggregation assays were performed by heating 5 µM Alcohol dehydrogenase (ADH) to 50° C. directly in a spectrophotometer using a thermostated cuvette holder in a total reaction volume of 500 µl. Absorbance was monitored at 360 nm ($A_{360}$) for 1200 seconds and readings were taken at every 100 seconds interval. When the $A_{360}$ values were plotted against time (black triangle) it was observed that absorbance increased with time reaching near saturation level at the 1200 sec time point. The increase in absorbance indicates aggregation of ADH. When Hsp16.3 was incorporated by mixing ADH with Hsp16.3 at a molar ratio of 5:4 the extent of aggregation decreased about 5 fold (black circle) indicating that Hsp 16.3 offers protection against aggregation (chaperon activity). Then the same experiment was performed in the presence of increasing concentrations of the Hsp16.3 binding peptide Seq ID 10 which is derived from the phage displayed peptide sequence (Seq ID 9) by adding the mandatory Gly-Gly-Gly-Ser linker at the C-terminal end: 25 µM (white square), 50 µM (black square) and 100 µM (white triangle). When the $A_{360}$ values at the saturation point were compared it was found that in the presence of 100 µM of peptide nearly 70% aggregation was restored, indicating that the concerned peptide was capable of inhibiting the chaperon activity of Hsp16.3. However the same effect may be obtained if the peptide instead of inhibiting the activity of Hsp16.3 promotes the aggregation of ADH. To eliminate such a possibility a control experiment was done in which the peptide alone was added to ADH. The resulting curve (white circle) shows that presence of peptide does not influence the aggregation of ADH. Hence it is claimed that the concerned peptide functions by directly inhibiting the activity of Hsp16.3.

To obtain a more quantitative interpretation of the data the % residual chaperon activity of Hsp 16.3 in the presence of different concentrations of inhibitor was derived as follows, the $A_{360}$ values at the saturation point (1200 secs) being taken into consideration.

| $A_{360}$ of heat treated ADH = | a |
| $A_{360}$ of heat treated ADH in the presence of Hsp16.3 = | b |
| $A_{360}$ of heat treated ADH in the presence of Hsp 16.3 and peptide (Seq ID 10) = | c |

Hence % chaperon activity of Hsp16.3 after addition of peptide = 100 × (a − c)/(a − b)

Figure 2B:
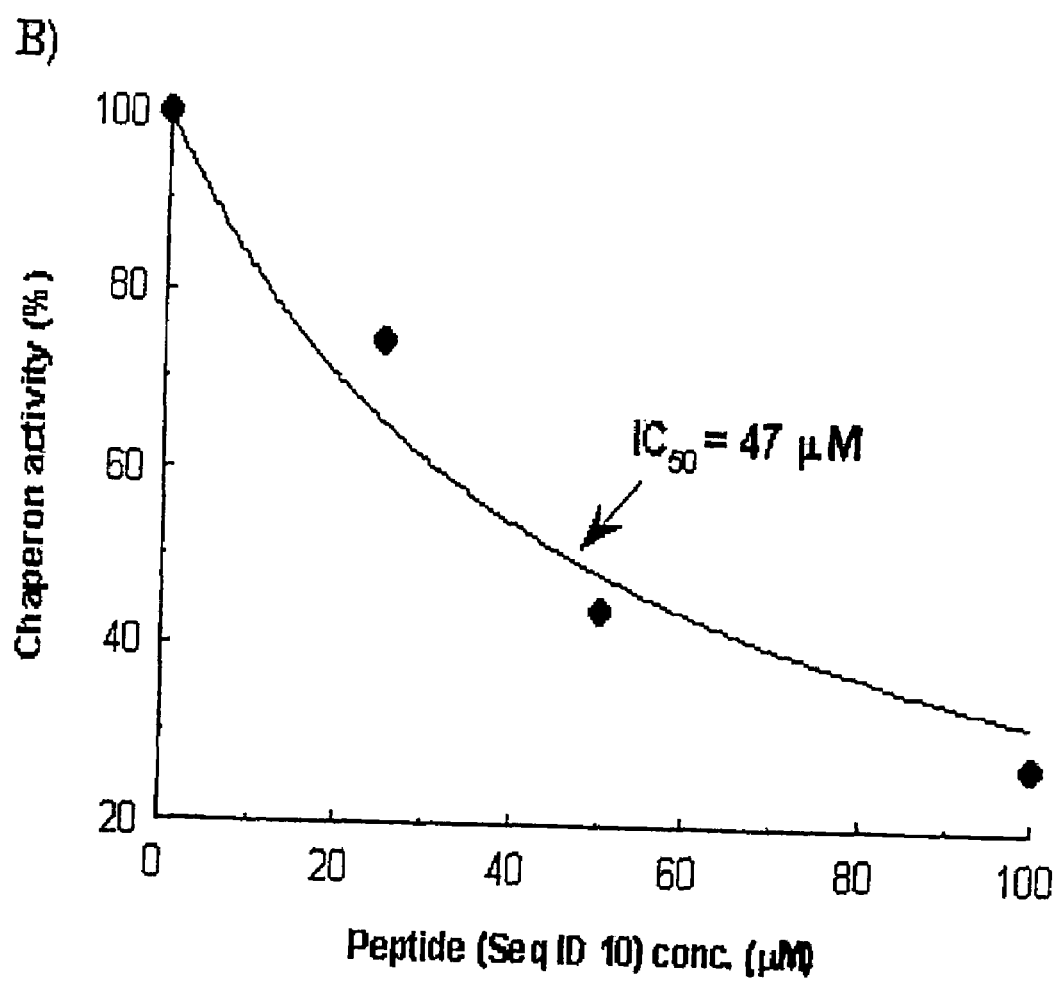

The % chaperon activity was then plotted against peptide concentration (FIG. 2B). From the resulting curve it is apparent that chaperon activity decreases exponentially with increasing concentration of peptide. The concentration of peptide at which 50% inhibition was observed i.e. $IC_{50}$ was determined. In case of peptide of Seq ID 10 the $IC_{50}$ was found to be about 47 µM. Using a similar experimental approach the corresponding value in case of peptide of Seq ID 22 was found to be 52 µM. The results support the claim that these synthetic peptides Seq ID 10 and 22 can inhibit the chaperon activity of Hsp16.3 and the $IC_{50}$, a parameter generally used as a measure of the inhibitory activity of an inhibitor under a given set of assay conditions, is in the range of 50 µM.

Example 5

Specific Inhibition of Hsp 16.3 Activity by the Peptides:

ADH upon being heated to 50° C. aggregates. This aggregation can be completely stopped when Hsp16.3 is added in such a way so as to obtain a molar ratio of ADH to Hsp 16.3 monomer of about 5:4. Incorporation of peptide at a concentration of 100 µM i.e. about 25 fold molar excess leads to significant inhibition of chaperon activity. The same assay can be used to demonstrate that the identified binding peptides, obtained after biopanning on Hsp16.3, specifically inhibit Hsp16.3 and not other related proteins present in the human host. Since it has been shown that Hsp16.3 has functional similarity with human alphaB-crystallin, an eye lens protein (Valdez et al., 2002), therefore the effect of these peptides on human alphaB-crystallin was examined. To demonstrate this aspect of the work, human alphaB-crystallin was obtained from Dr. K. P. Das of the Department of Chemistry, Bose Institute. The vector used for expression of this protein was originally generated by Dr. W. C. Boelens of the Nymegen Center for Molecular Life Sciences University of Nijmegen, 6550 HB Nijmegen, The Netherlands. Consent has been taken from the concerned scientists regarding the use of the recombinant protein specifically in the context of this disclosure. When an inhibition assay was done it was found that the peptide did not show any significant inhibition of the chaperon activity of alphaB-crystallin (FIG. 3).

An example to show the specificity of the inhibitory peptides for Hsp16.3 and not for alphaB-crystallin—a component of human eye lens. A similar assay as described in FIG. 2 was performed using alphaB-crystallin instead of Hsp16.3. The molar ratio between ADH and alphaB-crystallin was maintained at 5:4 as in the case of Hsp16.3. Aggregation in the absence of alphaB-crystallin (black triangle). Aggregation in the presence of alphaB-crystallin (black circle). The same experiment was performed in the presence of increasing concentrations of the Hsp16.3 binding peptide (Seq ID 10) 25 µM (white square), 50 µM (black square), 100 µM (white triangle). Only peptide control (ADH+100 µM peptide) (white circle). The % chaperon activity obtained in the presence of the peptide was plotted against peptide concentrations (FIG. 3B) as described in FIG. 2. The resulting curve shows that there was no inhibition of chaperon activity of alphaB-crystallin in the presence of increasing concentrations of peptide and hence the observed inhibition by the peptide is as claimed specific for Hsp16.3 and not the related human eye lens protein alphaB-crystallin. Similar results were obtained in case of peptide of Seq ID 22.

Example 6
Binding Activity of the Peptides as Determined by Fluorescence Anisotropy:

Peptides (corresponding to Seq IDs 9 and 21) were synthesized by the solid-phase method with the standard 9-flurenyl-methoxycarbonyl (Fmoc) chemistry with a mandatory Gly-Gly-Gly-Ser sequence added at the C-terminal to obtain peptides corresponding to Seq IDs 10 and 22 respectively. The C-terminal of the resulting peptides was amidated. The peptides were labeled by conjugation with FITC. Anisotropic titrations were done by adding increasing amounts of Hsp16.3 to a fixed amount of labeled peptide (200 nM). From such anisotropic titrations it was found that these peptides interact with an approximate $K_d$ of 50 μM and 40 μM respectively.

A part of this invention is the determination of binding affinity of these peptides by conjugating them with FITC and determining binding constant by determining increase in fluorescence anisotropy upon the addition of the Hsp16.3 to the fluorescein conjugated peptide. It was measured in Hitachi F 3010 spectrofluorometer having a facility for spectra addition and subtraction. The excitation and emission band passes were 5 nm unless mentioned otherwise. Anisotropy measurements were performed using a Hitachi polarizer accessory. The steady state fluorescence anisotropy (A) was calculated according to the following equation:

$$A=(I_{II}-GI_{1})/(I_{II}+2GI_{1})$$

Where, $I_{II}$ is the intensity when the polarizers were in the same direction, $I_1$ is the intensity when the polarizers were crossed, and G is the grating factor that corrects for wavelength-dependent distortion of the polarizing system. FITC-labeled peptides were titrated with increasing concentration of Hsp16.3 protein in 50 mM sodium phosphate buffer, pH 7.5, containing 300 mM NaCl at room temperature. The curve fittings were done using Kyplot (Koichi Yoshioka, 1997-1999, version 2.0 beta 4). By this technique the $K_d$ value of Seq ID 10 was determined to be ~50 μM and that of Seq ID 22 to be ~40 μM.

Determination of affinity constant by using fluorescence anisotropy. Titration of fluoresceinated peptide (Seq ID 22) at a concentration of 200 nM with increasing concentrations of Hsp16.3. The line shown is the best fit to a single-site binding equation. Each point is an average of three independent measurements. The solution conditions were 50 mM sodium phosphate buffer, pH 7.5, containing 300 mM NaCl. The temperature was 25±1° C. Excitation and emission wavelengths were 495 and 520 nm, respectively. By this technique the $K_d$ value of Seq ID 22 for Hsp16.3 was determined to be ~40 μM. In the same way the $K_d$ value of Seq ID 10 for Hsp16.3 was found to be ~50 μM (FIG. 4). The results indicate that the affinity of the synthetic peptides for the target — Hsp16.3 is nearly same.

Example 7
NMR Spectroscopy:

All NMR spectra were taken in a Bruker DRX-500 NMR spectrometer equipped with a Z-field gradient probe. All measurements were done in high precision 5-mm NMR tubes in 20 mM sodium phosphate buffer, pH 7.0, containing 250 mM NaCl in 90% $H_2O$ and 10% $D_2O$. All NMR experiments were done at 4° C., unless stated otherwise. TOCSY spectra were measured using standard pulse sequences in the Bruker pulse library using WATERGATE water suppression method. Standard Bruker software (Xwin-NMR version 1.3) was used to acquire and process the NMR data. The NMR samples were adjusted to a protein concentration of 0.1 mM and a 20-fold ligand excess (2 mM) over binding sites was used throughout the studies.

The comparison of chemical shifts of amide protons of free peptide (Seq ID 10) (A) and peptide with Hsp16.3 protein (B). Resonance assignments are indicated with a one-letter amino acid code. All NMR spectra were taken in a Bruker DRX-500 spectrometer equipped with a Z-field gradient probe. All measurements were done in high precision 5-mm NMR tubes in 20 mM sodium phosphate buffer, pH 7.0, containing 250 mM NaCl in 90% $H_2O$ and 10% $D_2O$ at 4° C. TOCSY spectra were measured using standard pulse sequences in the Bruker pulse library using WATERGATE water suppression method. Standard Bruker software (Xwin-NMR version 1.3) was used to acquire and process the NMR data. The NMR samples were adjusted to a protein concentration of 0.1 mM and a 20-fold ligand excess (2 mM) over binding sites was used throughout the studies. A significant chemical shift occured in both histidines denoted as H residues. This result confirms that the peptide interacts with the Hsp16.3 and that this interaction specifically involves the Histidine residues. Hence by inference it follows that any modification by which such interactions are strengthened would lead to more efficient inhibitor of the target protein -Hsp 16.3.

Example 8
Determination of Peptide Concentration by Fluorescamine Test:

As the peptide of Seq ID 10 does not contain any aromatic amino acid, the concentration of the peptide was determined by fluorescamine test. Fluorescamine (4-phenylspiro[furan-2(3H), 1-phthalan]-3,3-dione) (Sisco Research Laboratory, Mumbai, India) is a nonfluorophor compound, but whenever it reacts with primary amines including amino acids, peptides, proteins it becomes a fluorophor of which excitation wavelength is 390 nm and emission wavelength is 475 nm. One volume of fluorescamine in acetone (0.1 mg/mL) was mixed with three volumes of peptide (labeled or unlabeled) buffered with 0.2 M sodium borate (pH-7). Using a peptide of known concentration (e.g. Seq ID 22) as standard the concentration of this peptide was determined.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. An isolated peptide antagonist having the amino acid sequence of SEQ ID NO: 10 and SEQ ID NO: 22, for inhibiting chaperone activity of Heat shock protein 16.3 (Hsp 16.3).

2. The peptide as claimed in claim 1, wherein the peptide having the amino acid sequence of SEQ ID NO: 10 has a dissociation constant $K_d$ value of about 50 μM and the peptide having the amino acid sequence of SEQ ID NO: 22 has a dissociation constant $K_d$ value of about 40 μM.

3. The peptide as claimed in claim 1, wherein said peptide does not inhibit the activity of alpha-B crystallin protein.

* * * * *